(12) United States Patent
Okawa

(10) Patent No.: US 7,530,978 B2
(45) Date of Patent: May 12, 2009

(54) OPTICAL HAIR REMOVING DEVICE

(75) Inventor: Kazumi Okawa, Hikone (JP)

(73) Assignee: Matsushita Electric Works, Ltd., Osaka (JP)

( * ) Notice: Subject to any disclaimer, the term of this patent is extended or adjusted under 35 U.S.C. 154(b) by 0 days.

(21) Appl. No.: 11/984,348

(22) Filed: Nov. 16, 2007

(65) Prior Publication Data

US 2008/0119829 A1    May 22, 2008

(30) Foreign Application Priority Data

Nov. 16, 2006  (JP) ............................. 2006-309834

(51) Int. Cl.
*A61B 18/18* (2006.01)
(52) U.S. Cl. .............. 606/9; 606/10; 606/12; 607/88; 607/91
(58) Field of Classification Search .............. 606/3–28; 607/88–92; 128/898
See application file for complete search history.

(56) References Cited

U.S. PATENT DOCUMENTS

| 6,733,492 | B2 * | 5/2004 | Ota et al. ....................... 606/9 |
| 7,282,060 | B2 * | 10/2007 | DeBenedictis et al. ........ 607/88 |
| 2005/0177139 | A1 * | 8/2005 | Yamazaki et al. .............. 606/9 |
| 2006/0200114 | A1 | 9/2006 | Ferren et al. |
| 2007/0084057 | A1 * | 4/2007 | Shalev et al. ................. 30/34.2 |

FOREIGN PATENT DOCUMENTS

| JP | 2002-172179 | 6/2002 |
| WO | 98/51235 | 11/1998 |
| WO | 2006/003646 | 1/2006 |

* cited by examiner

*Primary Examiner*—Ahmed M Farah
(74) *Attorney, Agent, or Firm*—Bacon & Thomas, PLLC

(57) ABSTRACT

An optical hair removing device includes a light emitting unit for emitting a light and an irradiation unit for irradiating the light emitted from the light emitting unit to body hairs on a skin. Further, the optical hair removing device includes a control unit for controlling the light emission unit. The irradiation unit has a movement detection unit for detecting a movement of the irradiation unit on a skin and a contact detection unit for detecting a contact between the irradiation unit and the skin.

9 Claims, 3 Drawing Sheets

OPTICAL HAIR REMOVING DEVICE

FIELD OF THE INVENTION

The present invention relates to an optical hair removing device for removing body hairs on a skin by irradiating a light thereon.

BACKGROUND OF THE INVENTION

A conventional optical hair removing device includes a laser source for emitting a laser beam, an irradiation unit for irradiating the laser beam emitted from the laser source to body hairs on a skin, a moving mechanism for moving the irradiation unit along the contour of the skin in X and Y directions, and a control unit for controlling the moving mechanism.

The body hair is automatically removed by moving the irradiation unit on the skin in X or Y direction within a specific range with the use of the moving mechanism controlled by the control unit (see, e.g., Japanese Patent Laid-open Application No. 2002-172179).

Since, however, the moving mechanism moves the irradiation unit within the specific range under the control of the control unit in the optical hair removing device described in the patent application supra, it was difficult to detect the actual moving distance of the light irradiating unit on the skin.

Further, in the above optical hair removing device, a high power laser beam is used and, thus, the hairs can be removed even when the irradiation unit is positioned away from the skin by a certain distance. However, in a hair removing device using a low power flash lamp or the like, the irradiation unit needs to be located close to the skin when the light is irradiated. Moreover, the irradiation unit needs to be firmly contacted with the skin in order to prevent the light from leaking out and reaching user's eyes. In the prior art, however, it was difficult to confirm whether the irradiation unit makes a firm contact with the skin.

SUMMARY OF THE INVENTION

In view of the above, the present invention provides an optical hair removing device capable of directly detecting a movement of an irradiation unit on a skin and accurately detecting a contact between the irradiation unit and the skin.

In accordance with an embodiment of the present invention, there is provided an optical hair removing device including: a light emitting unit for emitting a light; an irradiation unit for irradiating the light emitted from the light emitting unit to body hairs on a skin; and a control unit for controlling the light emission unit, wherein the irradiation unit has a movement detection unit for detecting a movement of the irradiation unit on the skin and a contact detection unit for detecting a contact between the irradiation unit and the skin.

Further, the movement detection unit may be a roller encoder and the contact detection unit may include a contact switch.

Further, the irradiation unit may have a light detection unit for detecting the light emitted from the light emitting unit and light that enters from outside to the irradiation unit through a gap between the irradiation unit and the skin when the irradiation unit is made to contact with the skin.

Further, the light detection unit may be a photoelectric sensor.

Furthermore, after the light detection unit detected the light emitted from the light emitting unit, the control unit may allow the light emitting unit to emit light again if the movement detection unit detects the movement of the irradiation unit on the skin, and the contact detection unit detects the contact between the irradiation unit and the skin.

In the embodiment of the present invention, the movement detection unit directly and accurately detects an actual movement of the irradiation unit on the skin. Therefore, it is possible to prevent light from being irradiated on the same spot of the skin multiple times, which reduces burden to the skin. Further, the contact detection unit accurately detects the contact between the irradiation unit and the skin. Accordingly, even when light having low irradiation energy is used, the hair can be effectively removed. Also, it is possible to avoid that light is let out through a gap between the irradiation unit and the skin.

The movement detection unit is a roller encoder, and the contact detection unit includes contact switches. Therefore, the movement of the irradiation unit on the skin or the contact between the irradiation unit and the skin can be detected with a simple configuration.

By providing the light detection unit at the irradiation unit, the light emission in the light emitting unit can be detected. Further, when the irradiation unit is made to contact with the skin with a gap therebetween, it is possible to detect light entering from the outside to the irradiation unit through the gap. In that case, by stopping the light emission, it is possible to prevent the emitted light from reaching user's eyes.

When the light detection unit is the photoelectric sensor, the light amount can be detected with a simple and small-sized configuration.

After the light emitting unit emits light, the light emission is performed again if the movement detection unit detects the movement of the irradiation unit and the contact detection unit detects the firm contact between the irradiation unit and the skin. As a result, it is possible to prevent the light from being irradiated on the same spot of the skin multiple times, thereby reducing burden to the skin.

BRIEF DESCRIPTION OF THE DRAWINGS

The objects and features of the present invention will become apparent from the following description of embodiments, given in conjunction with the accompanying drawings, in which.

DETAILED DESCRIPTION OF THE EMBODIMENT

Embodiments of the present invention will now be described in detail with reference to the accompanying drawings which form a part hereof.

Figure 1:
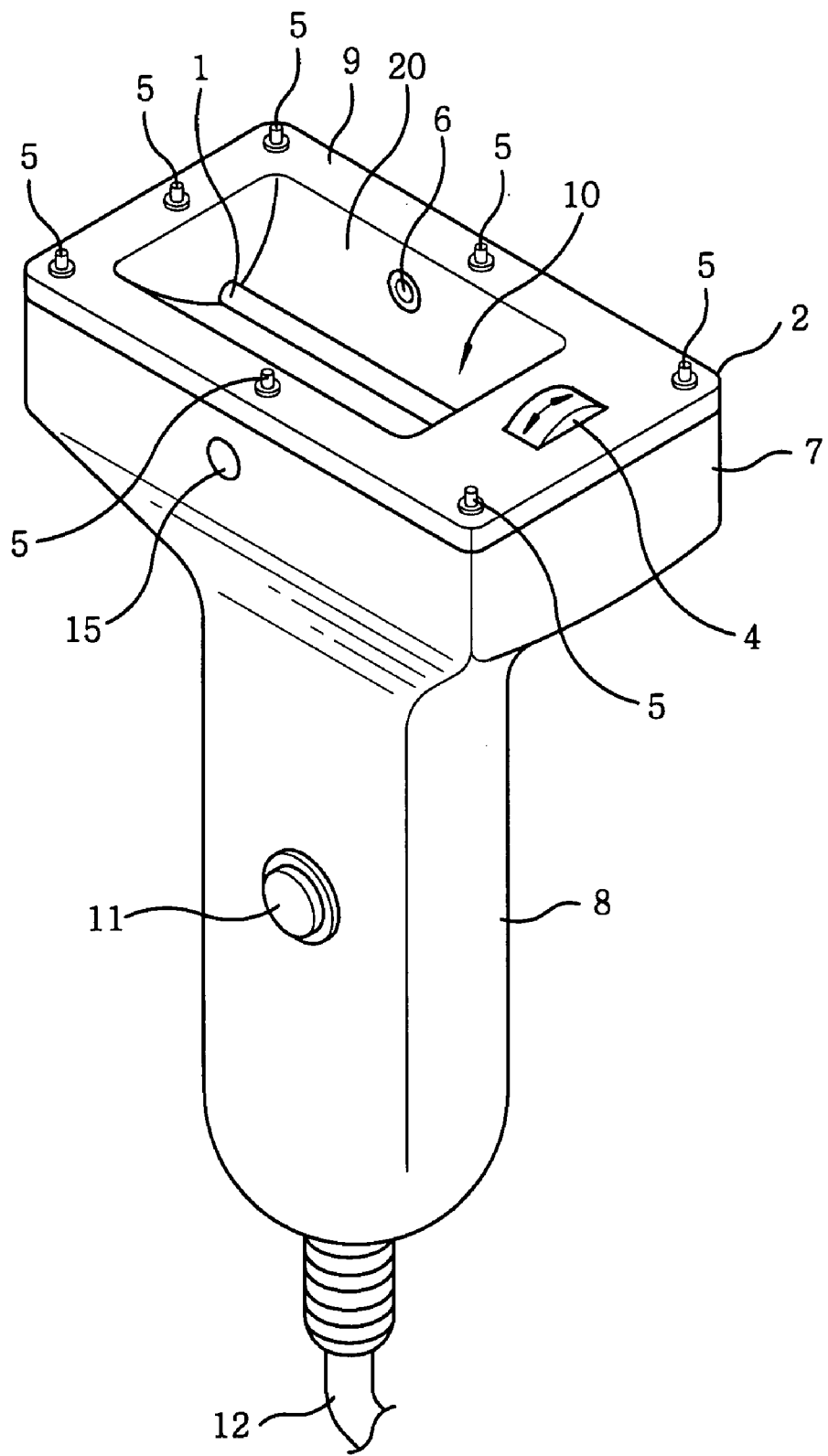
FIG. 1 shows a perspective view of an optical hair removing device in accordance with an embodiment of the present invention.
Figure 2:
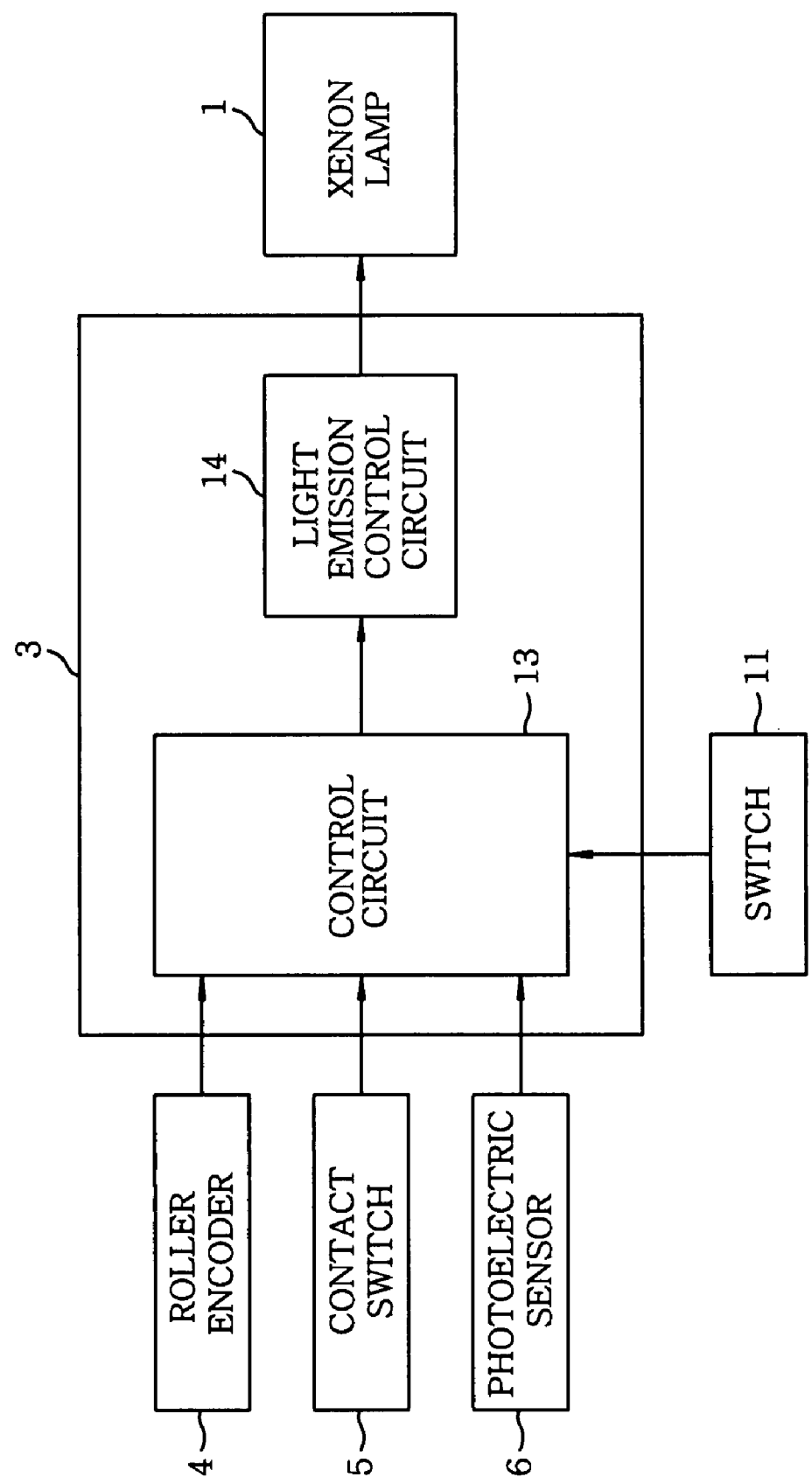
FIG. 2 describes a control block diagram of the optical hair removing device.

FIGS. 1 and 2 illustrate an optical hair removing device in accordance with an embodiment of the present invention. As shown in FIGS. 1 and 2, the optical hair removing device includes a light emitting unit 1, e.g., a Xenon lamp or the like, for emitting a light; an irradiation unit 2 for irradiating the light emitted from the Xenon lamp 1 to body hairs on a skin; a control unit 3 for controlling the light emission of the Xenon lamp 1. The irradiation unit 2 has a movement detection unit 4, e.g., roller encoder or the like, for detecting a movement of the irradiation unit 2 on the skin; and contact switches 5 serving as a contact detection unit for detecting a contact between the irradiation unit 2 and the skin.

Installed in the irradiation unit 2 is a light detection unit 6, e.g., photoelectric sensor or the like, for detecting the amount of light emitted from the Xenon lamp 1 and/or the amount of light entering from the outside to the irradiation unit 2 through the gap between the irradiation unit 2 and the skin when the irradiation unit 2 is made to contact with the skin.

After the photoelectric sensor 6 detected the light emitted from the Xenon lamp 1, the control unit 3 allows the Xenon lamp 1 to emit light again if the roller encoder 4 detects the movement of the irradiation unit 2 on the skin, and the contact switches 5 detects the contacts between the irradiation unit 2 and the skin.

Hereinafter, the optical hair removing device of this embodiment will be described in further detail. Referring to FIG. 1, the optical hair removing device includes a body case 7 and a grip portion 8 to be gripped by a user provided at a lower portion of the body case 7.

Provided at an upper portion of the main case 7 is the irradiation unit 2 for irradiating the emitted light to body hairs on the skin of the user. The irradiation unit 2 has on a top surface thereof a contact surface 9 to be contacted with the skin of the user. Further, a plurality of contact switches 5 for detecting the contact between the contact surface 9 and the skin of the user are installed on a peripheral portion of the contact surface 9 of the irradiation unit 2.

The roller encoder 4 for detecting the movement of the contact surface 9 on the skin is provided at one side of the contact surface 9 in the length direction thereof. A recess 10 having a specific opening area and depth is formed at a side of the roller encoder 4. The Xenon lamp 1 for emitting light is installed on a bottom portion of the recess 10. The roller encoder 4 is vertically floatable. A reflecting plate 20 for reflecting the light emitted from the Xenon lamp 1 is disposed at the inner side surfaces of the recess 10.

Disposed on a side portion of the recess 10 is the photoelectric sensor 6 capable of detecting the light emitted from the Xenon lamp 1 or the light that enters from the outside through the gap between the contact surface 9 and the skin when the contact surface 9 is made to contact with the skin of the user.

Further, a switch 11 for turning on the Xenon lamp 1 is provided on a side of the grip portion 8. Connected with a bottom of the grip portion 8 is a power cord 12 for supplying power to the optical hair removing device.

The control unit 3 for controlling the light emission of the Xenon lamp 1 is installed inside the body case 7. Further, the control unit 3 includes a light emission control circuit 14 connected with the Xenon lamp 1 to control light emission of the Xenon lamp 1, and a control circuit 13 connected with the roller encoder 4, the contact switches 5, the photoelectric sensor 6 and the switch 11. The control circuit 13 and the light emission control circuit 14 are formed of a CPU, a memory, an I/O and the like.

Figure 3:
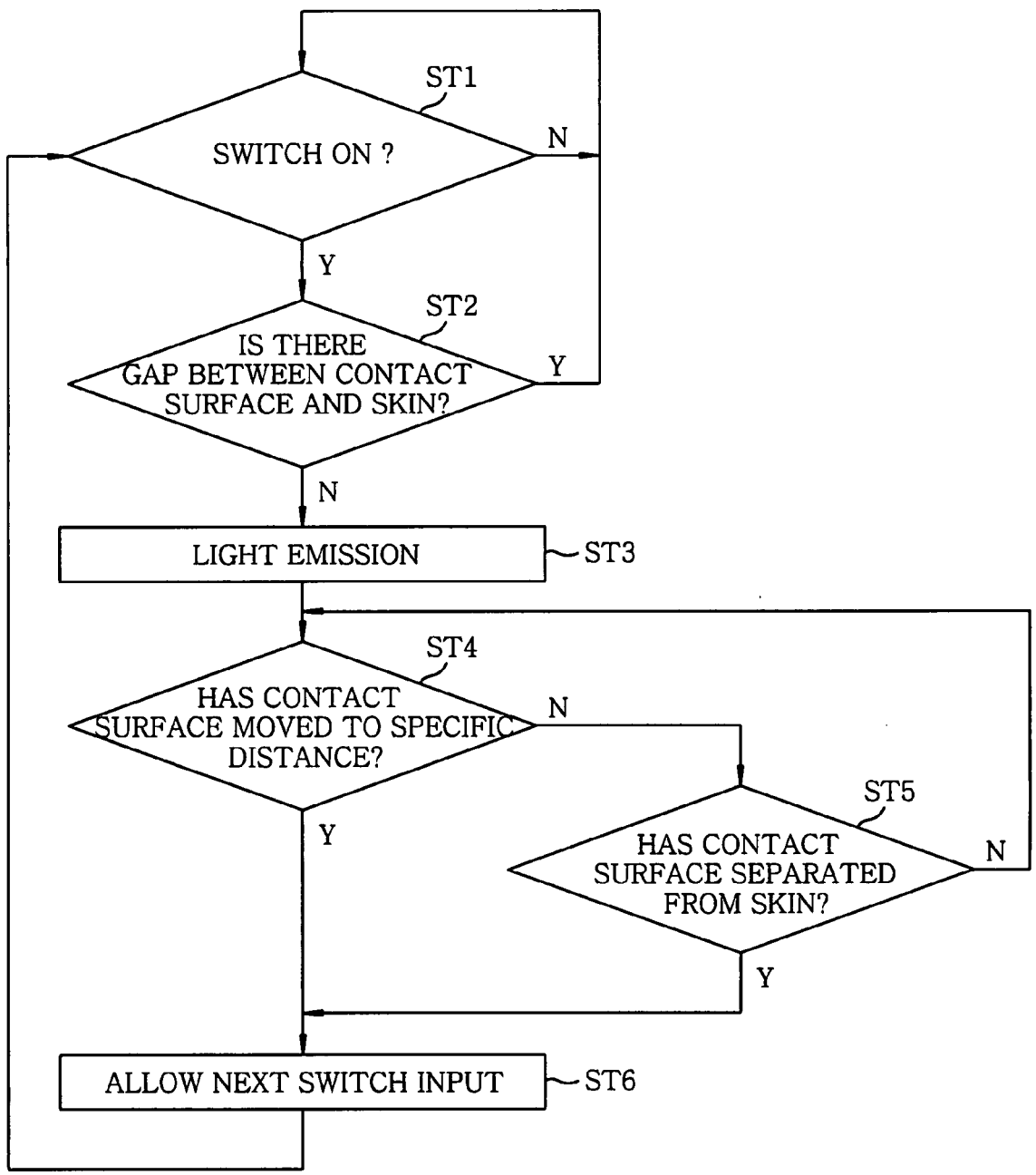
FIG. 3 provides a control flow chart of the optical hair removing device.

Hereinafter, an operation of the optical hair removing device in accordance with an embodiment of the present invention will be described with reference to FIGS. 1 to 3.

After plugging in the power cord 12 into a wall socket, for example, the user grips the grip portion 8 provided at the lower portion of the body case 7 and then contacts the contact surface 9 of the irradiation unit 2 provided at the upper portion of the body case 7 to the skin where body hairs need to be removed. By firmly pressing the contact surface 9 onto the skin, the contact surface 9 makes a close contact with the skin.

After checking that the contact surface 9 is firmly contacted with the skin, the user presses down the switch 11 provided at the side of the grip portion 8. Meanwhile, the control unit 3 determines whether the switch 11 is in the "ON" state (step ST1). If it is determined that the switch 11 is in the "ON" state (Y in the step ST1), the control unit 3 determines whether there is a gap between the contact surface 9 and the skin (step ST2). If the contact surface 9 is in the close contact with the skin, all of the contact switches 5 arranged on the contact surface 9 would be ON and the photoelectric sensor 6 provided at the side portion of the recess 10 would not detect light since no light would enter from the outside into the recess 10. Hence, the control unit 3 determines that no gap exists between the contact surface 9 and the skin if all the contact switches 5 are "ON" and at the same time the photoelectric sensor 6 does not detect light (N in step ST2). Thereafter, the light emission control circuit 14 of the control unit 3 controls the Xenon lamp 1 to emit light, and the light is irradiated to remove the body hairs on the skin (step ST3).

On the other hand, if the contact surface 9 is not in firm contact with the skin, all or part of the contact switches 5 arranged on the contract surface 9 would not be ON, or light would enter from the outside into the recess 10 since there would be a gap between the contact surface 9 and the skin. Hence, the control unit 3 determines that a gap exists between the contact surface 9 and the skin if at least one of contact switches 5 are not "ON" or the photoelectric sensor 6 detects the light (Y in step ST2). Then, the light emission control circuit 14 of the control unit 3 controls the Xenon lamp 1 not to emit light and the procedure returns to step ST1.

Though the use of the contact switches 5 and the photoelectric sensor 6 employed in accordance with the embodiment of the present invention, the Xenon lamp 1 can be made to emit light only when the contact surface 9 is in firm contact with the skin, i.e., only when there exists no gap therebetween. Accordingly, it is possible to prevent the light emitted from the Xenon lamp 1 from being leak out and reaching user's eyes through the gap between the contact surface 9 and the skin.

The light of the Xenon lamp 1 is emitted only for a very short period of time as in the case of a camera flash and, thus, the irradiation energy thereof is very low, without imposing burden of excessive heat or the like on the skin of the user. The optical hair removing device may have notifying unit 15, e.g., a sound generator (e.g., piezoelectric vibrator) or an LED, generating a sound or light when Xenon lamp 1 is turned on to thereby notify the user that light emission is made in due course.

When the light emission is completed, the user releases the contact between the contact surface 9 and the skin and then slides the contact surface 9 along the skin to an area where the next hair removal is needed. Next, the contact surface 9 is made to be in firm contact with the skin of the corresponding area.

At this time, if the roller encoder 4 provided on the contact surface 9 of the irradiation unit 2 detects a movement of equal to or greater than a specific distance, the control unit 3 determines that the contact surface 9 has properly moved to the area where the next hair removal is needed (Y in step ST4). Then, the control circuit 13 of the control unit 3 is allowed to accept a next switch "ON" signal from the switch 11 (step ST6).

If the roller encoder 4 does not detect the movement of equal to or greater than the specific distance (N in step ST4) after the light emission is completed and all of the contact switches 5 are OFF, the control unit 3 determines that the user has separated the contact surface 9 from the skin and has moved the contact surface 9 to the area where the next hair removal is needed (Y in step ST5). As a consequence, the control circuit 13 of the control unit 3 is allowed to accept the input signal from the switch 11 (step ST6).

Meanwhile, if the roller encoder 4 does not detect the movement up to the specific distance (N in step ST4) and not all of the contact switches 5 are OFF, the control unit 3 determines that the user has neither separated the contact surface 9 from the skin nor moved the contact surface 9 sufficiently (N in step ST5). Accordingly, the control circuit 13 of the control unit 3 is not allowed to accept the next input from the switch 11.

As described above, after the light is irradiated onto the skin, the control unit 3 allows the light to be emitted again only when the contact surface 9 has moved on the skin equal to or greater than specific distance or the contact surface 9 has been separated from the skin. As a result, the light can be prevented from being irradiated on the same spot on the skin multiple times, thereby preventing excessive burden to the skin.

In accordance with the embodiment of the present invention, there is provided an optical hair removing device having the roller encoder 4 and the contact switches 5. Due to the presence of the roller encoder 4, the actual movement of the contact surface 9 of the irradiation unit 2 on the skin can be directly and accurately detected with a simple configuration. Therefore, it is possible to prevent light from being irradiated on the same spot of the skin multiple times, which reduces burden to the skin. Further, due to the presence of the contact switches 5, the contact between the contact surface 9 and the skin can be accurately detected with a simple configuration. Accordingly, even when light having a low irradiation energy is used, the hairs can be effectively removed. Also, it is possible to ensure the firm contact between the irradiation unit 2 and the skin.

Furthermore, by providing the photoelectric sensor 6 in the recess 10 of the irradiation unit 2, it is possible to detect the light emitted from the Xenon lamp 1. Also, when the contact surface 9 of the irradiation unit 2 is made to contact with the skin with a gap therebetween, it is possible to detect the light entering the irradiation unit 2 through the gap. In that case, the light emission is not allowed, so that the light can be prevented from being emitted from the Xenon lamp 1 and reaching user's eyes.

Further, once the light is irradiated onto the skin, the control unit 3 allows the light to be emitted again only when the contact surface 9 has moved on the skin equal to or greater than the specific distance or the contact surface 9 has been separated from the skin. Hence, the light can be prevented from being irradiated on the same spot on the skin multiple times, thereby preventing excessive burden to the skin.

In the above embodiment of the present invention, the Xenon lamp 1 serves as the light emitting unit. However, a mercury lamp, a metal hydride lamp or the like can also be used as the light emitting unit.

As for the movement detection unit, the roller encoder 4 is used in the above embodiment. However, movement in X and Y directions can be detected by using, e.g., a trackball detecting rotation of the ball about two axis. Besides, a photoelectric encoder using a photoelectric device or the like can also be used as the movement detection unit.

As for the contact detection unit having plural contact sensors, the contact switches 5 are used as the contact sensors in the above embodiment. However, a proximity sensing photoelectric sensors or sensors for measuring an electric resistance of a skin by using electrodes or the like can also be used as the contact sensors. Further, irregularities on a skin surface of a user may be detected based on detection patterns of the sensors. For example, an armpit, a foot or the like can be identified based on the detection patterns. The light emission may not be allowed when a face is detected.

As for the light detection unit, the photoelectric sensor 6 is used in the above embodiment. However, a small-sized camera may be employed as the light detection unit, so that the amount of light can be further controlled in detail by detecting a skin color or the like.

While the invention has been shown and described with respect to the embodiments, it will be understood by those skilled in the art that various changes and modification may be made without departing from the scope of the invention as defined in the following claims.

What is claimed is:

1. An optical hair removing device comprising:
a light emitting unit for emitting light;
an irradiation unit for irradiating the light emitted from the light emitting unit to body hairs on a skin; and
a control unit for controlling the light emission unit,
wherein the irradiation unit has a movement detection unit for detecting a movement of the irradiation unit on the skin, a contact detection unit for detecting a contact between the irradiation unit and the skin, and a light detection unit for detecting the light emitted from the light emitting unit and light that enters from outside to the irradiation unit through a gap between the irradiation unit and the skin when the irradiation unit is made to contact with the skin, and
the control unit allows the light emitting unit to emit light if the light detection unit indicates that no light enters through the gap, when the light emitting unit is not emitting light.

2. The optical hair removing device of claim 1, wherein the movement detection unit is a roller encoder.

3. The optical hair removing device of claim 1, wherein the contact detection unit includes contact switches.

4. The optical hair removing device of claim 1, wherein the light detection unit is a photoelectric sensor.

5. The optical hair removing device of claim 1, wherein after the light detection unit detected the light emitted from the light emitting unit, the control unit allows the light emitting unit to emit light again if the movement detection unit detects the movement of the irradiation unit on the skin, and the contact detection unit detects the contact between the irradiation unit and the skin.

6. The optical hair removing device of claim 1, wherein the control unit controls the light emitting unit to emit light discontinuously.

7. The optical hair removing device of claim 5, wherein the control unit does not check the movement detected by the movement detection unit when the light emitting unit lights for the first time.

8. The optical hair removing device of claim 1, further comprising a switch for turning on the light emitting unit,
wherein after the light emitting unit emitted light, the control unit accepts a next turn on signal from the switch only if the movement detection unit detects the movement of the irradiation unit on the skin, or the contact detection unit detects a separation between the irradiation unit and the skin.

9. The optical hair removing device of claim 8, wherein after the control unit accepted the next turn on signal from the switch, the control unit allows the light emitting unit to emit light if the contact detection unit detects the contact between the irradiation unit and the skin.

* * * * *